United States Patent [19]
Zelaya

[11] Patent Number: 5,376,374
[45] Date of Patent: Dec. 27, 1994

[54] ORAL RINSE COMPOSITION

[76] Inventor: Luz M. Zelaya, 605 W. Curtis St., Linden, N.J. 07036

[21] Appl. No.: 66,470

[22] Filed: May 24, 1993

[51] Int. Cl.⁵ .................. A61K 35/78; A61K 7/26; C07D 305/12; C01G 9/02
[52] U.S. Cl. ................... 424/195.1; 514/901; 514/902; 514/725; 424/58; 549/408; 549/315; 423/622
[58] Field of Search ............ 424/195.1, 58; 514/901, 514/902

[56] References Cited

U.S. PATENT DOCUMENTS 4,382,886  5/1983  Sosmowski .................. 260/107

Primary Examiner—John W. Rollins
Assistant Examiner—Howard C. Lee
Attorney, Agent, or Firm—Otto S. Kauder

[57] ABSTRACT

There is disclosed a pleasant tasting oral rinse composition and a method of using the same. The composition consists essentially of cayenne pepper, calendula, echinacea, goldenseal, propolis, vinegar, and water in certain proportions.

9 Claims, No Drawings

ORAL RINSE COMPOSITION

FIELD OF THE INVENTION

This invention relates to a pleasant tasting oral rinse composition formulated with herbal and other natural ingredients.

PRIOR ART

The oral hygiene procedures of most people include a rinse of the mouth. For many, a rinse with fresh water is sufficient. Others prefer to include a rinse with a specially formulated product as a way to freshen the breath and control the bacterial population of the mouth. A popular product offered for killing germs that cause plaque, gingivitis, and so-called bad breath contains thymol, eucalyptol, methyl salicylate, and menthol as identified active ingredients along with water, nearly 30% alcohol, caramel color, and a preservative. The labels of two other products sold through large retail outlets list such ingredients as water, alcohol(17%), glycerine, sodium saccharin, sodium benzoate, cetyl pyridinium chloride, flavor, domiphen bromide, and color; and water, alcohol(15%), sorbitol, sodium lauryl sulfate, polysorbate 20, flavor, sodium saccharin, sodium chloride, and sodium citrate. Thus the use of synthetic chemicals is clearly evident in these products as antiseptics, surfactants, sweeteners, and preservatives, as is the presence of significant levels of alcohol.

Oral rinses are sometimes used professionally in dentistry and dental hygiene practice to mitigate irritation and minor bleeding resulting from dental procedures, mechanical cleaning of the teeth, or from gum diseases. Frequently, a patient with an infection of the gum has puffy red gums that may be bleeding and cause discomfort, and when the hygienist cleans the teeth to remove tartar or calculus, this may increase the discomfort. As a result, the very conditions that make the use of a special rinse more essential and necessary than the casual self-prescribed use of the conventional products also make people more sensitive to and irritated by some of the chemical ingredients and alcohol in the conventional products. These sensitivities and irritations can discourage patients from following a practitioner's recommendation to carry out a course of treatment with such a rinse for some time after an office visit. There remains, therefore, an unmet need for a product that patients, particularly patients suffering from gum diseases, will find agreeable to use over a period of time.

The increasing disenchantment among some people with the use of synthetic chemicals taken together with the more specific disadvantages of the conventional products cited above has focused interest on alternate products derived from herbal and other natural sources. Dr. Michael A. Weiner's book "The Herbal Bible: A Family Guide to Herbal Home Remedies" (published by Quantum Books, San Rafael Calif. 94912, copyright 1992) contains an alphabetical listing of "Diseases, Symptoms, and Suggested Remedies"; the entry under "Gums, sore, bleeding, or spongy" (page 47) recommends "The mouth should be rinsed three to four times a day with a decoction made from (recipe) no. 98." That recipe, "For Gargle and Mouthwash" appears on page 173, as follows:

| Item | | Drachms* |
|---|---|---|
| 1. | Wild Sage Leaves - expectorant, relieves inflammation | 10 |
| 2. | Marsh Rosemary - astringent | 10 |
| 3. | Goldthread - astringent especially valued for canker sores | 2 |
| 4. | Rhatany Root - astringent and tonic to the tissues | 2 |
| 5. | Cranesbill Root (Wild Geranium) - astringent and tonic | 6 |
| 6. | Red Oak Bark - astringent, mild antiseptic | 6 |
| 7. | Comfrey Root - an aromatic stimulant | 2 |
| 8. | Cloves - stimulant | 2 |

*1 drachm = approximately 5 grams or 1 teaspoon of liquid

Mix well and divide into 10 doses, using herbs especially cut for tea. Directions: Add one dose to a pint of boiling water, boil slowly for 5 minutes, let stand for about 10 minutes, then strain and add 1 tablespoon of table salt to the decoction. Use as a gargle and mouthwash every 2 to 3 hours, until the inflammation and swelling have subsided. If the decoction is found too astringent, it may be diluted with water.

With four astringent ingredients and a large amount of table salt, this recipe whatever its merits fails to satisfy the need for a pleasant tasting material that users will find acceptable for a course of treatment lasting days or even weeks.

The above recipe for gargle and mouthwash is also given in John B. Lust's "Herb Book" (Bantam Books, Toronto and New York, 1974) at page 484. In addition, Lust's book also includes an alphabetical list of conditions and affected organs with lists of herb materials recommended for each. There is no indication what quantities of the listed herbs are to be used, and whether singly or in combination. Following is the list given under the heading "GUMS: (Mostly as a mouthwash. For bleeding, see also HEMORRHAGE; for inflammation, see also INFLAMMATION)"

Barberry
Bennet
Bistort
Blackberry
Black currant
Comfrey
Dogwood
Echinacea
English walnut
Goldenseal
Myrrh
Periwinkle (both)
Pokeweed
Rhatany
Shave grass
Spotted cranebill
Watercress
Willow (all)
Witch hazel A product called "Mouth Tonic" has appeared in so-called health-food stores. According to the label, it contains myrrh, echinacea, goldenseal, and propolis. The product has a bitter taste.

A search of U.S. patents from 1971 to August 1992 revealed 161 patents containing mention of mouth rinse. None of these patents included mention of even one ingredient (other than water) of the essential ingredients of the composition of this invention. The search also revealed 139 patents containing mention of cayenne pepper or calendula or echinacea or goldenseal or propolis or vinegar, but none of these included mention of mouth rinse and none included mention of more than two of the listed ingredients. The following disclosures are illustrative.

Hangay et al U.S. Pat. No. 5,080,901 of Jan. 14, 1992 discloses an active ingredient composition comprising extracts of marigold (i.e. calendula), horse-chestnut, licorice, silver-weed, walnut-tree leaves, and Roman camomile oil, used for the treatment of hemorrhoids, sunburn, and dry and sensitive skin.

Deryabin U.S. Pat. No. 5,061,491 of Oct. 29, 1991 discloses a medicinal agent for treatment of mastitis in animals and humans comprising a mixture of a decoction and an ammonia-solution infusion of the herbs wild camomile, pot marigold, stringing nettle, common centaury, pine buds, common plantain, birch buds, pot marjoram, garden sage, garden angelica, dandelion, coltsfoot leaves, great burnet, common valerian, peppermint, common thyme, and tripartite bur-marigold.

Ismail U.S. Pat. No. 4,938,960 of Jul. 3, 1990 discloses an ointment containing vitamin E and calendula extract in an ointment base.

Fontaine U.S. Pat. No. 4,931,277 of Jun. 5, 1990 discloses a medication for treatment of alcoholic toxicomania comprising an extract of at least one of cayenne pepper and poplar bark or wood.

Chambers U.S. Pat. No. 4,906,461 of Mar. 6, 1990 discloses a hair treatment composition comprising epsom salt, sodium bicarbonate, sea kelp, placenta extract, cider vinegar and water.

Summers U.S. Pat. No. 4,887,620 of Dec. 19, 1989 discloses a tobaccoless chewing or snuff composition including 0.0001 to 0.005% cayenne pepper.

Novak U.S. Pat. No. 4,880,630 of Nov. 14, 1989 discloses a skin care composition having antiinflammatory and keratolytic activity comprising an extract of *Lycium halmifolium* optionally with addition of propolis.

Ayache U.S. Pat. No. 4,795,638 of Jan. 3, 1989 discloses a cosmetic composition to be applied to the skin in order to reduce or eliminate cellulite or fat build-up. The composition contains in an oily base, (1) a rubefacient, (2), at least one oil soluble plant extract from a plant chosen from the group comprising climbing ivy, arnica, rosemary, marigold, sage, ginseng, Saint Johns wort, ruscus, ulmaria, orthosiphon, and algae, and (3) a volatile organo polysiloxane. Substances which can be used as a rubefacient include capsicum extracts; nicotinic acid salts such as triethanolamine nicotinate; nicotinic acid esters such as methyl, ethyl, hexyl, phenyl, and benzyl nicotinate as well as alpha tocopherol nicotinate; nicotinyl alcohol and its organic acid esters such as for example nicotinyl tartarate or nicotinate.

Wilson U.S. Pat. No. 4,719,111 of Jan. 12, 1988 discloses a packing to be applied in the mitigation of bed sores comprising an admixture of lecithin, goldenseal root or rhizome, and myrrh gum.

Tabord U.S. Pat. No. 4,699,791 of Oct. 13, 1987 discloses an antiseptic composition for external use in lotions, tinctures, handkerchiefs, and shampoos consisting essentially of an aqueous-alcoholic extract of wine vinegar and honey with optional addition of tincture of propolis.

SUMMARY OF THE INVENTION

In accordance with this invention, a pleasant tasting oral rinse composition for professional as well as home use has been discovered, consisting essentially of cayenne pepper, calendula, echinacea, goldenseal, propolis, vinegar, and water in a liquid preparation. The term "consisting essentially of" is used to indicate that unspecified additional ingredients can be present but must not affect the useful and esthetic properties of the composition, and hence intensely bitter, astringent, or salty substances are excluded.

While agreeable in taste, the composition is of sufficient strength that the quantity that a person can conveniently hold in the mouth at one time is adequate for one home care treatment, and treatment need not be carried out more frequently than twice a day. The composition is used to relieve oral discomfort resulting from irritated, red, and bleeding gums, simple mouth blisters, cold sores, pizza burn, or cheek, lip, and tongue bites, as well as to freshen the breath and remove debris after dentistry or dental hygiene procedures, by inserting in the mouth a quantity of the rinse, suitably 2 to 10 milliliters, holding it in the mouth for a sufficient time, suitably one to two minutes, and removing the rinse, as by spitting out or swallowing the rinse and such amounts of saliva as have accumulated in the mouth under the stimulating effect of the rinse. When measured with standard medicine droppers, the quantity of the rinse is suitably 50 to 250 drops, most preferably 50 to 70 drops.

When used under professional supervision in the treatment of gum disease and periodontal involvement, larger quantities of the rinse composition can be administered, either by repeatedly introducing and removing mouthfuls of rinse or by a continuous irrigation technique over a period from a few minutes to an hour, which can be readily adapted to most dentists' chairs. Such use of the rinse composition can supplement such professional procedures as deep scaling and root planing to mitigate and alleviate the condition being treated, and stimulate and enhance the patient's natural healing mechanisms to the extent that surgical procedures otherwise required can be postponed and, in favorable cases, entirely avoided.

All the specified components of the rinse composition of this invention are essential to its providing the desired effect. In particular, water and vinegar together make up from about 67 to about 77 weight per cent of the composition, and the relative proportions of water and vinegar to each other are in the range from 5:2 to 2:5 by weight. The remaining essential ingredients calendula, cayenne pepper, echinacea, goldenseal, and propolis, in the form of liquid preparations, make up from about 23 to about 33 weight per cent of the composition.

DESCRIPTION OF PREFERRED EMBODIMENTS

The oral rinse composition of this invention is a liquid. It is not necessary for the liquid to be sparkling-clear. The liquid can be cloudy, and can contain oily droplets as well as particles of plant material. It is satisfactory as long as it can be made relatively uniform for dispensing by simple agitation such as shaking or stirring.

The provision of liquid preparations of calendula, cayenne pepper, echinachea, goldenseal, and propolis from the plant and beehive materials respectively follows conventional techniques and forms no part of this invention. Certain liquid preparations of each specified ingredient, especially tinctures, are commercially available and can be utilized in making the rinse composition of this invention with excellent results.

The whole or any part of the plant providing each of the herbal ingredients of the oral rinse composition of this invention can be used. All species of a particular plant, such as echinacea, are effective. Whole propolis as obtained from beehives can be used, as can such derived fractions as propolis wax, propolis resin, and propolis balsam.

In a preferred group of oral rinse compositions according to this invention, the herbal ingredients are selected from the plant species and parts shown in the following table:

| Ingredient | Plant parts | Plant species |
| --- | --- | --- |
| Calendula | flowers, fresh or dried | C. officinalis |
| Cayenne pepper | fruits, whole pods | Capsicum frutescens, C. annuum |
| Echinacea | rhizome, root | E. angustifolia, E. pallida, E. tennesseensis |
| Goldenseal | rhizome, root | Hydrastis canadensis |

Any vinegar can be used, including balsamic vinegar, cider vinegar, distilled vinegar, and wine vinegar. Apple cider vinegar is preferred.

The oral rinse composition of this invention can be prepared in any suitable way. Thus, the fresh or dried herbal ingredients and propolis can be chopped or ground and combined with water and vinegar in the desired proportions, steeped until extraction has occurred, and the liquid decanted and bottled for use. For improved precision and reproducibility, it is preferred to obtain a liquid preparation of each ingredient separately and then combine predetermined amounts of each preparation. Certain liquid preparations, particularly tinctures or alcohol-containing extracts, are commercially available and convenient to use.

By one preferred method, tinctures of calendula, cayenne pepper, echinacea, goldenseal, and propolis can be combined in desired proportions to give a homogeneous liquid concentrate that can be kept for long periods of time in closed containers and then blended with vinegar and water for ultimate use. The relative proportions of the specified ingredients are preferably within the range of 48 to 64 parts by weight of calendula, 8 to 12 parts by weight of cayenne pepper, 48 to 64 parts by weight of echinacea, 48 to 64 parts by weight of goldenseal, and 70 to 98 parts by weight of propolis.

Where alcohol-free preparations are preferred, these are best prepared under sterile conditions in order to provide preparations that can be kept without spoilage. Preparations by such traditional methods as infusion, decoction, and cold extraction are satisfactory, as are preparations by newer methods such as that of Herve et al U.S. Pat. No. 4,897,266 issued Jan. 30, 1990 whose disclosure is here incorporated by reference. Herve's method can be summarized as a combination of four operations, cryocomminution, molecular milling, decantation at high speed, and ultrafiltration, resulting in a sterile filtrate of high activity without the use of alcohol.

At the discretion of the supervising professional, such use of the rinse composition to assist healing of gums and other parts of the mouth are further improved and enhanced by conventional oral hygiene procedures and dietary supplements including minerals such as zinc and vitamins, particularly vitamins C, E, beta-carotene, and co-enzyme Q10.

The following Examples are provided to illustrate the invention without intending to limit its scope, which is defined by the appended claims.

EXAMPLE 1

The following were charged to a steam-sterilized vessel:

Tincture of calendula officinalis (active ratio 1/5, alcohol 65% by vol.) 56 milliliters Tincture of capsicum frutescens (cayenne pepper, active ratio 1/10, alcohol 75% by vol) 10 ml Tincture of echinacea purpurea and echinacea angustifolia (active ratio 1/1.8, alcohol 60% by vol). 56 ml Tincture of hydrastis canadensis (goldenseal root, active ratio 1/5, alcohol 40% by vol.) 56 ml Extract of propolis (alcohol-free, active ratio 1/10) 84 ml Apple cider vinegar 486 ml Distilled water 224 ml Agitation of this mixture for about 5 seconds produced a light tan cloudy liquid, characterized by a fruity and pleasantly spice-hot taste. This was kept agitated while being transferred into steam-sterilized 2 fl. oz. capacity (approx. 57 ml) brown glass bottles. These were then closed with plastic screw caps carrying an eye dropper and sealed with tamper-evident strips.

EXAMPLE 2

A male dental patient in his late thirties had moderate to severe periodontal involvement and had been advised by the dentist to have periodontal surgery.

Initial treatment consisted of deep scaling and root planing carried out by the dental hygienist and irrigation into perio pockets with successive 5 ml quantities of the rinse composition of Example 1 during a five minute period.

The same treatment was repeated eight days later. A third treatment was carried out 2 weeks after the first treatment and a fourth treatment 3 weeks after the first treatment.

The patient's home care consisted of twice daily flossing, brushing, and irrigation with a 5 ml syringe containing the rinse composition of Example 1. Home care also included the following dietary supplements:

Vitamin C 3000 milligrams daily
Vitamin E 400 international units twice daily
Zinc 50 milligrams twice daily
Beta carotene 30,000 international units daily
Co-enzyme Q10 150 to 200 milligrams daily Twelve weeks after the initial treatment, examination by the dental hygienist showed that the periodontal condition had been eliminated. The prognosis was judged to be very good. The patient's recall schedule for monitoring and dental hygiene was set for once every three months.

These favorable results demonstrate the unexpected advantages of the use of the oral rinse composition according to this invention.

EXAMPLE 3

A female dental patient approximately 36 to 42 years old had moderate to severe periodontal involvement and had been advised to undergo periodontal surgery.

Initial and subsequent treatments consisted of deep scaling, root planing, and irrigation into perio pockets with the rinse composition of Example 1. The patient was treated every 2 to 3 weeks for six months, after which recall appointments were extended to every 6 to 8 weeks.

The patient's home care consisted of twice daily flossing, brushing, and irrigation with a 5 ml syringe containing the rinse composition of Example 1. Home care also included the following dietary supplements:

Vitamin C 3000 milligrams daily
Vitamin E 400 international units twice daily
Zinc 50 milligrams twice daily
Beta carotene 30,000 international units daily
Co-enzyme Q10 150 to 200 milligrams daily Examination by the hygienist showed that the treatment has alleviated the periodontal condition and eliminated the need for surgery. Prognosis is very good. Recall appointments for monitoring and treatment have been extended to every 3 months without recurrence of periodontal involvement.

These gratifying results illustrate the unexpected advantages of the oral rinse composition in accordance with this invention.

EXAMPLE 4

A male patient in his late thirties had moderate to severe periodontal involvment and had been advised to have periodontal surgery.

Initial and subsequent treatments consisted of deep scaling, root planing, and irrigation into perio pockets with the rinse composition of Example 1. The patient was treated every 2-3 weeks for 4 months, after which recall appointments for further treatments were extended to every 3 months.

The patient's home care consisted of twice daily flossing, brushing, and irrigation with a 5 ml syringe containing the rinse composition of Example 1. Home care also included the following dietary supplements:

Vitamin C 3000 milligrams daily
Vitamin E 400 international units twice daily
Zinc 50 milligrams twice daily
Beta carotene 30,000 international units daily
Co-enzyme Q10 150 to 200 milligrams daily After fifteen months, examination by the hygienist found that the patient's periodontal condition was eliminated. No surgery was performed. Prognosis is very good. The patient's recall schedule for monitoring is every 4 to 6 months.

These favorable results demonstrate the unexpected advantages of using the oral rinse composition in accordance with this invention.

I claim:

1. A pleasant tasting oral rinse consisting essentially of
   a) cayenne pepper,
   b) calendula,
   c) echinacea,
   d) goldenseal,
   e) propolis,
   f) vinegar, and
   g) water
   in a liquid preparation, in which the proportions of ingredients f and g are in the range of 2:5 to 5:2 relative to one another and combined are in a proportion by volume of 67 to 77 parts f and g combined to 23 to 33 parts of a,b,c,d, and e total, and ingredients a, b, c, d, and e are present in relative proportions by weight of 8 to 12 parts of a, 48 to 64 parts of b, 48 to 64 parts of c, 48 to 64 parts of d, and 70 to 98 parts of e.

2. An oral rinse according to claim 1 in which ingredient f is apple cider vinegar.

3. A stable concentrate suitable for preparation of a pleasant tasting herbal rinse according to claim 1 comprising tincture of cayenne pepper, tincture of calendula, tincture of echinacea, tincture of goldenseal, and propolis.

4. The method of relieving oral discomfort comprising the steps of inserting in the mouth of a person in need of relieving oral discomfort a suitable quantity of oral rinse according to claim 1, holding said rinse in the mouth for a sufficient time, and removing said oral rinse from the mouth.

5. The method according to claim 4 in which the quantity of oral rinse is in the range from two to ten milliliters.

6. The method according to claim 4 in which the holding time in the mouth is in the range from 1 to 2 minutes.

7. The method of alleviating gum disease comprising the steps of inserting in the mouth of a patient in need of alleviating gum disease a suitable quantity of oral rinse according to claim 1, holding said rinse in the mouth for a sufficient time, and removing said oral rinse from the mouth.

8. The method of claim 7 in which the steps of inserting a quantity of oral rinse into the mouth, holding said oral rinse in the mouth, and removing said oral rinse from the mouth are repeated periodically for a period of time in the range from two weeks to four months.

9. The method of claim 7 further supplemented by the administration of dietary supplement comprising zinc, vitamin C, vitamin E, beta-carotene, and co-enzyme Q10.

* * * * *